(12) United States Patent
von Seck

(10) Patent No.: US 9,750,628 B2
(45) Date of Patent: Sep. 5, 2017

(54) MEDICAL DEVICE FOR COMBATING OVERWEIGHT OR OBESITY IN HUMANS

(71) Applicant: Peter von Seck, Wiesbaden (DE)

(72) Inventor: Peter von Seck, Wiesbaden (DE)

( * ) Notice: Subject to any disclaimer, the term of this patent is extended or adjusted under 35 U.S.C. 154(b) by 168 days.

(21) Appl. No.: 13/961,024

(22) Filed: Aug. 7, 2013

(65) Prior Publication Data

US 2014/0041670 A1 Feb. 13, 2014

(30) Foreign Application Priority Data

Aug. 9, 2012 (DE) .......... 10 2012 015 839

(51) Int. Cl.
*A61F 5/00* (2006.01)
*A61F 5/56* (2006.01)
*A61C 7/12* (2006.01)

(52) U.S. Cl.
CPC .............. *A61F 5/0006* (2013.01); *A61C 7/12* (2013.01); *A61F 5/56* (2013.01); *A61F 5/566* (2013.01)

(58) Field of Classification Search
CPC .............. A61F 5/0003; A61F 2005/563; A61F 5/0006; A61F 5/56; A61F 5/566; A63B 71/085; A61C 7/08; A61C 7/36; A61C 7/12
USPC ........................................................ 128/859
See application file for complete search history.

(56) References Cited

U.S. PATENT DOCUMENTS

| 4,738,259 | A | 4/1988 | Brown et al. |
| 5,899,691 | A | 5/1999 | Parker |
| 2003/0059737 | A1 | 3/2003 | Hall |
| 2009/0035729 | A1 | 2/2009 | Pele |
| 2011/0094522 | A1* | 4/2011 | Weisflog ............... 128/861 |

FOREIGN PATENT DOCUMENTS

| GB | 2433203 A | 6/2007 |
| NL | 2005541 C | 4/2012 |

OTHER PUBLICATIONS

Search Report and Written Opinion for the corresponding European application dated Jan. 8, 2014.

* cited by examiner

*Primary Examiner* — Kari Rodriquez
*Assistant Examiner* — Raymond E Harris
(74) *Attorney, Agent, or Firm* — Kilpatrick Townsend & Stockton LLP

(57) ABSTRACT

A medical device for combating overweight or obesity in humans by achieving a more rapid feeling of satiety utilizes a bite raiser which can be connected to the human maxilla and/or mandible and which covers at least some of the occlusal surface of the masticatory teeth. A splint adapted to tooth crowns equips at least some of the masticatory teeth with an occlusal elevation for reducing the size of the masticatory surface. The occlusal elevation overlies the cusp tips of a masticatory tooth in order to link the bite elevation to a spanning of the masticatory relief of the covered masticatory tooth.

8 Claims, 3 Drawing Sheets

MEDICAL DEVICE FOR COMBATING OVERWEIGHT OR OBESITY IN HUMANS

The invention relates to a device for combating overweight or obesity in humans.

GB 2 433 203 A discloses a medical device of the type in question for combating overweight or obesity in humans. According to said document, a bite raiser is provided which arranges a box-shaped structure securely over at least some of the masticatory teeth. A surface that covers the masticatory surface areas of the teeth like a lid is thus obtained as masticatory surface.

U.S. Pat. No. 4,738,259 discloses a weight control device that blocks the natural process of mastication. Lingual flanges are provided which prevent a movement of food to and from the area of mastication.

As is described in DE 10 2005 041 093 A1, obesity is a real problem facing civilization and is in most cases attributable to poor eating habits, lack of exercise, etc. It is known that poor eating habits of the kind that lead to obesity are the result of a lack of discipline on the part of the affected patients in relation to food. For this reason, these patients often fail to stick to diets, or the patients go back to their former eating habits after the end of the diet.

To solve these problems, it is therefore known to reduce the size of areas of the digestive tract, in particular the stomach, by surgery and to create a bypass connection to the small intestine. In this way, the patient experiences a sense of fullness even when relatively small portions of food have been taken, and this ultimately stops the patient from taking more food. For a reduction that causes the patient the least possible strain, clips can be placed by endoscopy at suitable positions on the inside face of an organ, a band is engaged in them and, by pulling the two free ends of the band together, the organ can be narrowed. The natural functions of the organs that have been changed in this way is not preserved, and therefore, in addition to the invasive burden on the patient, organ damage also arises.

The object of the invention is therefore to create a device for combating overweight or obesity in humans, which device corrects poor eating habits and can be used in a way that minimally impairs the patient.

This object is achieved by a medical device for combating overweight or obesity in humans by achieving a more rapid feeling of satiety, comprising a bite raiser which can be connected to the human maxilla and/or mandible and which covers at least some of the occlusal surface of the masticatory teeth, and that a splint adapted to tooth crowns is provided for the bite raiser, which splint equips at least some of the masticatory teeth with an occlusal elevation for reducing the size of the masticatory surface, which occlusal elevation overlies the cusp tips of a masticatory tooth in order to link the bite elevation to a spanning of the masticatory relief of the covered masticatory tooth.

A device for combating overweight or obesity in humans is thereby created that slows down the process of mastication. The slowing-down of the process of mastication results in an increased rate of chewing. The occlusal elevation according to the invention influences the mechanical process of mastication by changing the nature of the surface configuration of the masticatory surface, i.e. the occlusal surface, of a masticatory tooth. The full contact of the natural occlusal surface of a masticatory tooth is reduced in size. The rate of chewing therefore has to be increased to take in food.

Chewing is the mechanical processing of food by occlusal squeezing pressure. The teeth are the actual tools of the apparatus of mastication. The forces of mastication arise between their crowns. If, according to the invention, the masticatory surface is now reduced in size, more chewing movements are needed to mechanically process the food. A change is obtained in the time needed to take in food. The eating time for a meal is, for example, lengthened. The patient is forced to eat slowly since, instead of the usual 5 to 10 chewing movements, more chewing movements, for example 20 to 40 chewing movements, are needed to chew the same amount of food. The patient is trained to eat slowly.

According to the invention, it is further achieved that the intake of food during a meal is lengthened in such a way that the hormone-controlled feeling of satiety, which occurs some 15 to 30 minutes after eating, can already occur while food is being taken during a meal. The patient is therefore satiated, even though the amount of food eaten is smaller. The slow eating that is enforced according to the invention prevents overweight and leads to a sustained reduction of overweight.

The splint can be easily fitted and can be produced from different materials. The splint can be fitted temporarily during meals only and is therefore preferably designed to be removable. The splint preferably equips the first and second premolars and the first molar of the maxilla and/or mandible with an occlusal elevation. The occlusion movement of the jaw, with guidance of the teeth and masticatory surfaces, is not adversely affected by this. The final bite setting provides a sufficiently stable position of a mechanical occlusion.

Further embodiments and advantages of the invention are set forth in the following description and in the dependent claims.

The invention is explained in more detail below with reference to the illustrative embodiments depicted in the attached figures.

Figure 1:
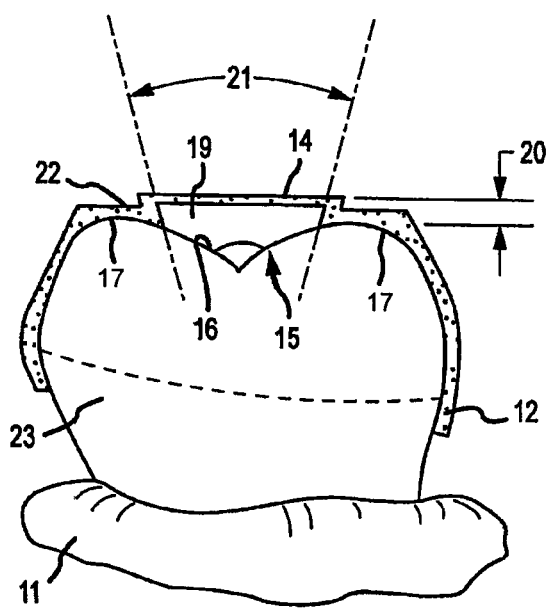
FIG. 1 shows a schematic cross section of a first molar with a splint according to the invention.
Figure 2:
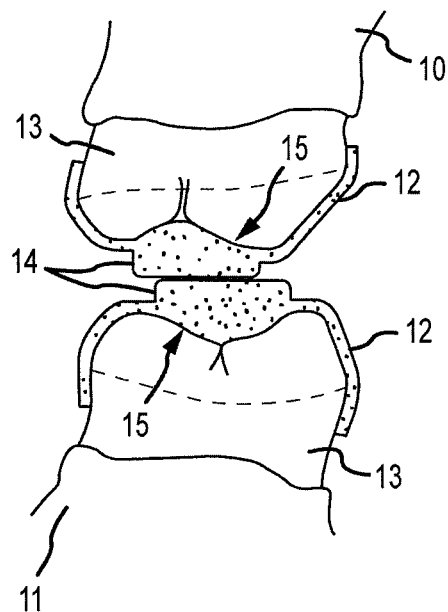
FIG. 2 shows a schematic cross section of an occlusal contact form of two masticatory teeth, with a splint according to the invention on the maxilla and mandible.
Figure 3:
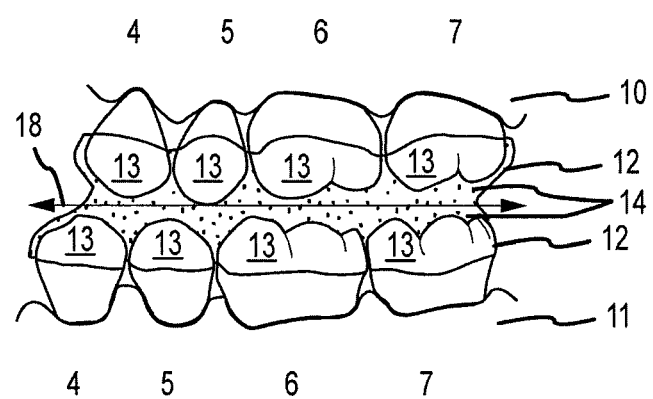
FIG. 3 shows a schematic side view of an occlusal contact form.

As FIG. 1 to FIG. 3 show, the invention relates to a medical device for combating overweight or obesity in humans by achieving a more rapid feeling of satiety. For this purpose, the device is designed as a splint 12 which can be connected to the human maxilla 10 and/or mandible 11 and which equips at least some of the masticatory teeth 13 with an occlusal elevation 14 for reducing the size of the masticatory surface. The splint 12 is an occlusal overlay (anchor) splint adapted to tooth crowns of the masticatory teeth 13, the tooth crown being the upper part of a tooth protruding from the gums.

Figure 4:
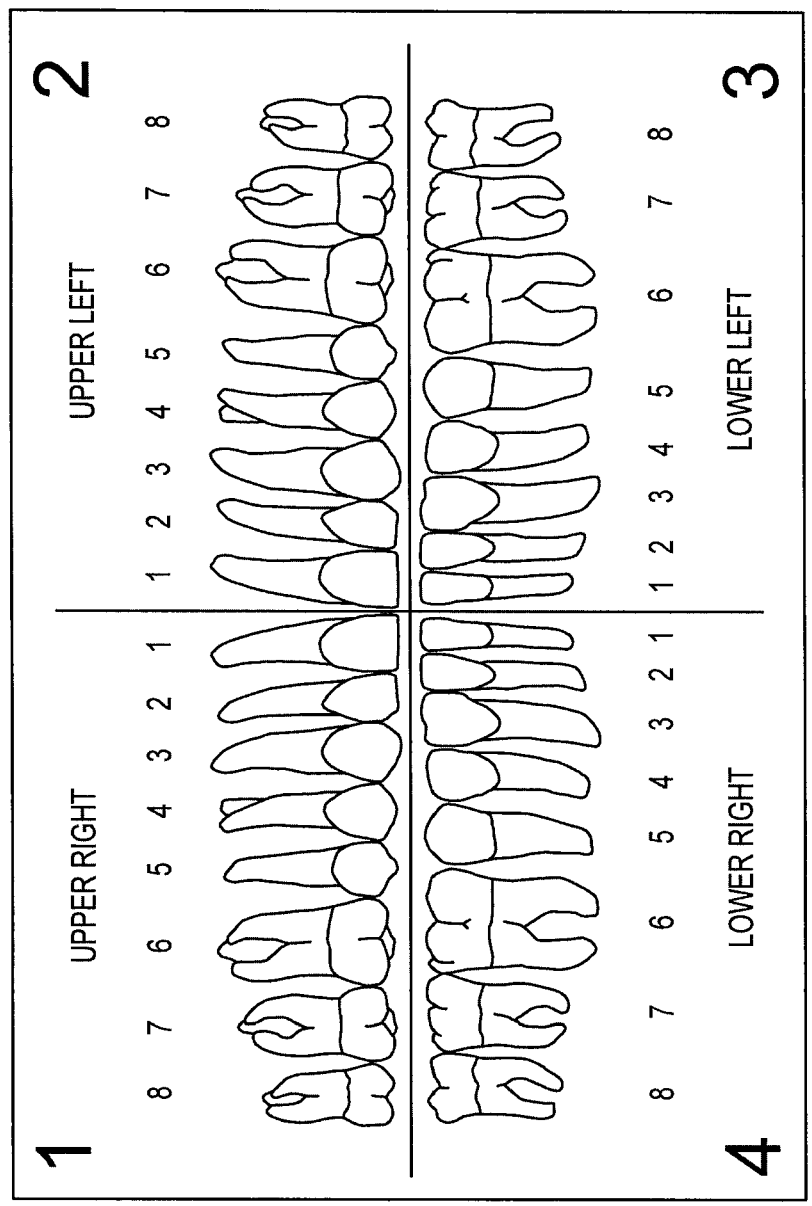
FIG. 4 shows the tooth chart of the permanent dentition numbered according to the old German system.

The masticatory teeth 13 named after their function are the premolars and molars, in each case to the right and to the left in the maxilla and mandible, which are also covered by the expression buccal teeth. According to FIG. 4, showing the old German system, the number 4 designates in each case the first premolar, the number 5 designates in each case the second premolar, and the numbers 6, 7 and 8 designate the first, second and third molars of the maxilla and mandible.

The masticatory teeth 13 have a masticatory relief for which the term masticatory surface 15 has become established, although it is not a surface but instead a system of cusps, crests, ridges and furrows. The function of the masticatory teeth is to insalivate and make smaller the morsels of food taken in with the front teeth. Through the contact of the upper and lower masticatory teeth 13 (buccal teeth) with each other, they fit harmoniously in each other in the natural occlusion and form the mastication centre.

This mastication centre is reduced in size by the splint 12, since the masticatory surface 15 receives an occlusal elevation 14 along at least some of the masticatory teeth 13. This elevation 14 can be designed such that the furrows 16 are filled at least partially or completely, as a result of which an almost plane masticatory surface is made available as a horizontal plane 18 by the occlusal elevation 14, as is shown in FIG. 1 and FIG. 3. The masticatory surface 15 is in this way already reduced. Moreover, the cusp tips 17 of a masticatory tooth 13 can be built over by the occlusal elevation 14, as is likewise shown in FIG. 1. A bite elevation 20 is hereby associated with a spanning of the masticatory relief.

The occlusal elevation 14 designs the bite elevation 20 preferably by a bar section 23 that is designed as a protruding section of splint 12. The width of the bar section 23 is preferably less than the width of the masticatory surface 15 over the cusp tips 17. Especially preferably the bar section 23 has a width which substantially covers each furrow 16 of a masticatory tooth 13 preferably centered. Via the setting of the width of the bar section 23 between the cusp tips 17 of a masticatory tooth 13 the height of the reduction of the masticatory surface can be chosen for each patient. The above description is valid for both a maxilla and a mandible as shown in FIG. 2.

The occlusal elevation 14 sets, for example, a bite elevation in the range of 0.5 to 2 mm per jaw 10, 11. By being able to choose the height and width of the occlusal elevation 14, it is possible to reduce the masticatory surface 15 by 10 to 50%, for example.

The splint 12 particularly preferably sets an occlusal elevation 14 in the area of the first and second premolars (4 and 5 according to FIG. 4) and of the first molar (6 according to FIG. 4) of the maxilla and/or mandible 10, 11. According to FIG. 4, an occlusal elevation 14 also extends over the second molar (7 according to FIG. 4).

The splint 12 can be made of plastic, metal or a ceramic material, wherein these materials can be the colour of teeth. These materials can be thermoformed, cast or milled for use. Also mixed, i.e. metal masticatory surfaces can be formed on a plastic splint. The thickness and nature of the splint 12 are adjustable. The thickness of the splint 12 is in the range of 0.3 to 0.5 mm preferably outside the elevation 14.

The occlusal elevation 14 can also be lined with a soft elastic material 19 (cf. FIG. 1). The soft elastic material is in particular silicone.

The splint 12 can preferably be fitted so as to be removable by the patient, such that the splint 12 may be worn only temporarily, in particular limited to the period of food intake. It is thus possible to dispel concerns of any kind regarding jaw changes or joint pain. The splint 12 can be supported by friction, by clasps or as model casting.

The occlusal elevation 14 can be provided with a kind of drainage system or channel 22 for saliva to flow off. As FIG. 1 shows, the elevation 14 is for this purpose bent off laterally for example, with an angle 21.

Finally, pressure-sensitive components can be built into the elevation 14 for diagnostic or therapeutic purposes in the area of the occlusion field. Moreover, the splint can be equipped with a transponder, in particular a passive transponder, which permits the identification of the splint.

The invention claimed is:

1. A medical device for combating overweightness or obesity in humans by achieving a more rapid feeling of satiety, comprising:
    a lower splint;
    an upper splint that is configured to reduce a masticatory surface by covering masticatory teeth of the human maxilla and/or mandible, the upper splint comprising:
    a splint body having an artificial occlusal surface that is configured to be positioned over the masticatory teeth between upper and lower teeth rows, wherein the artificial occlusal surface is configured to be positioned over and placed into direct contact with at least a portion of a natural occlusal surface of the masticatory teeth, wherein the artificial occlusal surface defines a surface area that is smaller than a natural occlusal surface area to reduce the size of the natural occlusal surface area during chewing, and wherein the artificial occlusal surface is built up by an occlusal elevation to define a saliva channel to facilitate drainage of saliva from the splint and to form a final blocking position between the upper and lower teeth rows, wherein the occlusal elevation defines a masticatory surface that is configured to come into direct contact with food when chewing, and wherein the masticatory surface is spaced apart from the artificial occlusal surface; and
    opposing sidewalls configured to wrap around a portion of the human maxilla and/or mandible to couple the splint to the human maxilla and/or mandible;
    wherein the entire splint body, including the artificial occlusal surface, the occlusal elevation, and the opposing sidewalls are a single, homogeneous solid piece of the same material and includes no holes or voids to reduce the size of the natural occlusal surface such that it takes more time to eat food when wearing the splint; and
    wherein the occlusal elevation is configured as a protruding bar section of the splint, wherein the width of the bar section is less than the width of the masticatory surface over the cup tips, and wherein the bar section has a length sufficient to extend along the first and second premolars and the first molar of the maxilla and/or mandible such that the final bite setting provides a sufficiently stable position of a mechanical occlusion; and
    wherein the upper splint is unconnected to the lower splint so as to not interfere with the user's chewing motion when chewing food.

2. The medical device according to claim 1, wherein the occlusal elevation comprises first and second straight walls that form the protruding bar section to facilitate chewing.

3. The medical device according to claim 2, wherein the first and second straight walls are angled.

4. The medical device according to claim 1, wherein the artificial occlusal surface is spaced apart from the masticatory surface by 0.3 mm to 0.5 mm.

5. The medical device according to claim 1, wherein the upper and lower splints are made of plastic, metal or a ceramic material.

6. The medical device according to claim 1, wherein the upper splint is supported by friction, supported by clasps, or supported as model casting.

7. The medical device of claim 1, wherein the masticatory surface is 10-50% of the area of the artificial occlusal surface.

8. A method for combating overweightness or obesity in humans using the device as claimed in claim 1 by achieving a more rapid feeling of satiety, the method comprising:

coupling the splint of claim 1 to masticatory teeth of the human maxilla and/or mandible, wherein the splint reduces a masticatory surface with the artificial occlusal surface that forms a final blocking position between upper and lower teeth rows, wherein the artificial occlusal surface is positioned over at least a portion of a natural occlusal surface of the masticatory teeth; and chewing food with the splint, wherein the masticatory surface comes into direct contact with food when chewing and also reduces the size of the natural occlusal surface such that it takes more time to eat food when wearing the splint.

\* \* \* \* \*